United States Patent
Schultheis et al.

(10) Patent No.: US 10,254,535 B2
(45) Date of Patent: Apr. 9, 2019

(54) ILLUMINATION SYSTEM COMPRISING HETEROGENEOUS FIBER ARRANGEMENT

(71) Applicant: SCHOTT AG, Mainz (DE)

(72) Inventors: Bernd Schultheis, Schwabenheim (DE); Hubertus Russert, Jugenheim (DE); Holger Werner, Frankfurt (DE); Kevin Tabor, Webster, MA (US)

(73) Assignee: SCHOTT AG, Mainz (DE)

( * ) Notice: Subject to any disclaimer, the term of this patent is extended or adjusted under 35 U.S.C. 154(b) by 0 days.

(21) Appl. No.: 15/690,535

(22) Filed: Aug. 30, 2017

(65) Prior Publication Data

US 2018/0081165 A1  Mar. 22, 2018

(30) Foreign Application Priority Data

Aug. 31, 2016 (DE) .................. 10 2016 216 443

(51) Int. Cl.
| | |
|---|---|
| *G02B 6/06* | (2006.01) |
| *G02B 23/24* | (2006.01) |
| *A61B 1/00* | (2006.01) |
| *G02B 23/26* | (2006.01) |
| *F21V 8/00* | (2006.01) |

(52) U.S. Cl.
CPC ........ *G02B 23/2469* (2013.01); *A61B 1/0017* (2013.01); *A61B 1/00165* (2013.01); *A61B 1/00167* (2013.01); *G02B 6/0008* (2013.01); *G02B 6/06* (2013.01); *G02B 23/2423* (2013.01); *G02B 23/2446* (2013.01); *G02B 23/2453* (2013.01); *G02B 23/26* (2013.01); *G02B 6/0006* (2013.01)

(58) Field of Classification Search
CPC ........................................... G02B 6/06
USPC .......................................... 385/33
See application file for complete search history.

(56) References Cited

U.S. PATENT DOCUMENTS

| | | | |
|---|---|---|---|
| 3,089,484 A | 5/1963 | Hett | |
| 3,615,313 A | 10/1971 | Phaneuf | |
| 3,801,181 A * | 4/1974 | Kitano | A61B 1/00163 359/652 |
| 3,902,880 A | 9/1975 | Strack | |

(Continued)

FOREIGN PATENT DOCUMENTS

| | | |
|---|---|---|
| DE | 2028111 | 12/1970 |
| DE | 102010052479 | 5/2012 |

(Continued)

*Primary Examiner* — Kaveh C Kianni
(74) *Attorney, Agent, or Firm* — Ohlandt, Greeley, Ruggiero & Perle, L.L.P.

(57) ABSTRACT

An illumination system is provided that includes a spatial fiber arrangement with an optical element at the distal end of the fiber arrangement. The fiber arrangement has a first region including individual fibers with a significantly smaller active diameter in comparison with the individual fibers of a remaining region. The optical element at the distal end is assigned the remaining region. The fiber arrangement can be a rigid fiber rod that includes an intermediate region provided between the first region and the remaining region. The intermediate region suppresses stray light transfers between the first and remaining regions. The fiber arrangement can include an optical coupling element at a proximal end of the fiber rod.

21 Claims, 3 Drawing Sheets

(56) References Cited

U.S. PATENT DOCUMENTS

| | | | |
|---|---|---|---|
| 4,281,929 A * | 8/1981 | Lord | G02B 23/26 356/241.1 |
| 4,732,448 A * | 3/1988 | Goldenberg | A61B 18/245 385/117 |
| 4,772,093 A | 9/1988 | Abele | |
| 4,784,144 A * | 11/1988 | Ono | A61B 1/00165 385/117 |
| 4,790,295 A * | 12/1988 | Tashiro | A61B 1/00096 600/176 |
| 4,854,302 A * | 8/1989 | Allred, III | A61B 1/042 348/65 |
| 5,116,317 A | 5/1992 | Carson, Jr. | |
| 5,550,945 A * | 8/1996 | Gregory | G02B 6/06 385/116 |
| 5,951,543 A * | 9/1999 | Brauer | A61B 18/201 606/10 |
| 6,178,346 B1 * | 1/2001 | Amundson | A61B 5/0086 348/77 |
| 6,487,326 B1 | 11/2002 | Pantano | |
| 6,547,721 B1 * | 4/2003 | Higuma | A61B 1/121 600/109 |
| 6,571,118 B1 * | 5/2003 | Utzinger | A61B 5/0071 356/318 |
| 6,678,541 B1 * | 1/2004 | Durkin | G01N 21/474 600/309 |
| 7,304,724 B2 * | 12/2007 | Durkin | G01N 21/31 356/326 |
| 2001/0038453 A1 * | 11/2001 | Jung | G01J 3/02 356/419 |
| 2001/0043330 A1 * | 11/2001 | Jung | G01J 1/06 356/419 |
| 2002/0003620 A1 * | 1/2002 | Jung | A61B 5/0088 356/73 |
| 2002/0007111 A1 * | 1/2002 | Deckert | G02B 23/2407 600/177 |
| 2002/0021869 A1 * | 2/2002 | Griffin | A61B 18/22 385/43 |
| 2002/0024653 A1 * | 2/2002 | Jung | G01J 3/02 356/73 |
| 2002/0135752 A1 * | 9/2002 | Sokolov | A61B 5/0075 356/39 |
| 2005/0259254 A1 * | 11/2005 | Soller | G01J 3/08 356/328 |
| 2006/0030753 A1 | 2/2006 | Boutellette | |
| 2007/0280612 A1 * | 12/2007 | Treado | A61B 1/00165 385/115 |
| 2008/0044146 A1 * | 2/2008 | Weisser | G02B 6/06 385/119 |
| 2010/0020320 A1 * | 1/2010 | Yao | G01J 3/2803 356/319 |
| 2013/0156389 A1 * | 6/2013 | Shinji | A61B 1/00167 385/103 |
| 2013/0301999 A1 | 11/2013 | Russert | |
| 2014/0242538 A1 | 8/2014 | Senn | |
| 2015/0016140 A1 | 1/2015 | Weingaertner | |
| 2015/0305602 A1 * | 10/2015 | Gal | A61B 1/00167 600/112 |
| 2017/0052319 A1 | 2/2017 | Schultheis | |
| 2017/0055840 A1 * | 3/2017 | Toriyama | A61B 5/0084 |
| 2017/0082534 A1 * | 3/2017 | Toriyama | A61B 1/00039 |

FOREIGN PATENT DOCUMENTS

| | | |
|---|---|---|
| DE | 102013208838 | 3/2015 |
| EP | 2891467 | 7/2015 |
| WO | 2013050589 | 4/2013 |
| WO | 2015073370 | 5/2015 |
| WO | 2016066370 | 5/2016 |

* cited by examiner

ILLUMINATION SYSTEM COMPRISING HETEROGENEOUS FIBER ARRANGEMENT

CROSS REFERENCE TO RELATED APPLICATIONS

This application claims benefit under 35 U.S.C. § 119(a) of German Patent Application No. 10 2016 216 443 filed Aug. 31, 2016, the entire contents of which are incorporated herein by reference.

BACKGROUND OF THE INVENTION

1. Field of the Invention

The invention relates to an illumination system for an inspection system, which comprises a spatial fiber arrangement with an optical element at the distal end of the fiber arrangement, and wherein the fiber arrangement has in its cross section at least one region B having individual fibers with a significantly smaller active diameter in comparison with the individual fibers of a remaining region A of the fiber arrangement, and wherein the optical element at the distal end corresponds in particular to said region B. The illumination system is connected to a light source and/or is at least connectable to such a light source and/or assignable thereto. The invention as well comprises the combination of the illumination system in combination with the light source.

2. Description of Related Art

Such inspection systems are known from the field of endoscopy. In this case, a surface that is usually difficult to access and is intended to be inspected is illuminated with light, usually white light, by means of a flexible or rigid endoscope. Via complex lens systems, the light reflected back is guided out of the endoscope via separate channels and is projected into a camera system. Such endoscopic systems are used in particular in the field of equipment or machinery inspection, e.g. for inspecting motors or aircraft engines, on the one hand, and on the other hand in the field of medical technology, here in particular for minimally invasive procedures. Moreover, such devices in the medical sector have to be able to be disassembled and reconditioned. Reconditioning methods that may be mentioned here include in particular cleaning and/or disinfection methods using strongly basic solutions and sterilization by means of autoclaving at a temperature of up to 135° C. and typical vapor pressures of approximately 3 bar. In particular rigid or flexible fiber arrangements comprising fibers made of glass or quartz glass are therefore suitable. Such endoscopes generally are therefore very cost-intensive and complex to produce, particularly if high-resolution images of the surface are intended to be transmitted.

In the dental sector, devices for curing dental fillings are known, inter alia, in which intensive blue light is guided via optical fiber rods to the tooth to be treated, as is described e.g. in WO 015073370 A1 and WO 2013/050589 A2.

EP 2891467 A1 describes a bent fiber rod incorporated as a light guide in a turbine housing of a dental drill, wherein image information is feedable to a camera. Said light guide has a lens at the coupling-out end of the fiber rod. Here, too, the motivation consists in enabling easy monitoring of the tooth surface.

From the applicant, approaches are known, inter alia, which make it possible to realize fiber arrangements having extremely small fibers for image transmission. Such image guides comprise several tens of thousands of individual fibers and allow resolutions of typically 3 to 6 µm.

US 2008/0044146 A1 discloses for example a flexible fiber arrangement comprising a fiber bundle with a region designed as an image guide and a region designed as a light guide. At the distal end an optical lens system is assigned to the region of the fiber bundle that is designed as an image guide.

DE 10 2010 052479 A1 describes a fiber arrangement and a method for producing such an arrangement, for less complex, comparatively cost-effective rigid image guides.

DE 10 2013 208 838 B4 in the name of the applicant discloses fiber rods having in particular improved optical properties in the blue spectral range, which enables applications in the dental sector.

DE 10 2013 219 039 A1 describes fiber rods in which an optical element made of highly transparent LSR (Liquid Silicone Rubber) is arranged at the fiber rod end.

For many applications in the industrial and/or medical sector and/or for analytical purposes, a less complex, lower-resolution image of the surface and/or of the volume to be inspected is sufficient to ensure in particular a surface modification or alteration and/or positioning monitoring, without the need to use cost-intensive complex optical systems such as are used in prior art endoscopic systems.

SUMMARY

Therefore, it is a purpose of the invention to provide an illumination system, in particular a fiber arrangement, which can be used to realize a less complex and cost-effective camera- or sensor-based inspection solution.

The purpose of the invention is achieved by virtue of the fact that the fiber arrangement is designed as a rigid fiber rod, and that a region C is provided between the region A and the region B, said region C suppressing stray light transfers between the regions A and B of the fiber rod. An optical coupling element can be provided at the proximal end of the fiber rod, by means of which optical coupling element, in the operating state, light from the light source can be coupled into the fiber rod and an image at the proximal end of the fiber rod from the region B can be coupled into a camera or into a sensor. Region C allows improvement of the image quality in a surprisingly simple way. In particular, the usually very intensive light for illumination from the image guiding channel through the region B can be shielded from the camera and/or the sensor.

With such a heterogeneous fiber rod, it is possible, on the one hand to illuminate objects to be inspected and, on the other hand, to evaluate the image reflected back for monitoring a surface with regard to modifications or conspicuous features or position monitoring. This fiber rod additionally allows the camera to be able to be arranged at a distance from the object to be inspected, which is advantageous particularly in the case of expected ambient conditions with regard to moisture and temperature. For medical-applications, this allows the fiber arrangement to be able to be subjected to cleaning and autoclaving processes for reconditioning. By means of this heterogeneous fiber arrangement with a region with a fiber diameter usually used for light guiding (region A) and at least one region with significantly reduced individual fiber diameter (region B) for image guiding, it is possible moreover to reduce the production effort in comparison with an approach with a reduced individual fiber diameter over the entire diameter of the fiber rod. With such fiber rods it is possible to produce in particular so-called dental curing rods (or dental rods for short) which, after treatment of the patient, can easily be demounted from the curing device and be reconditioned or sterilized. In applications in the industrial sector, it is thus possible to realize less complex bushings, e.g. in machine interiors, motors, engines or heating systems, with less assembly efforts. It is as well possible to inspect the quality of connections in connection technology. For analytical purposes and/or water monitoring, it is as well possible to quantify and, if appropriate, characterize the presence of bodies in the liquid.

In one preferred embodiment variant of the invention, it is provided that an individual fiber core diameter B in the region B of the fiber rod has a diameter of less than 25 µm, typically of 10 to 20 µm, preferably less than 10 µm. Thus, images of the object surface which have a sufficiently good resolution can be projected onto the camera at least in a simple manner. The individual fiber core diameter A in the region A of the fiber rod is usually 40 to 100 µm diameter.

Various methods are appropriate for the production of such fiber rods, which also comprise the repeated redrawing of fibers. Depending on the production process, the region B can be designed as a substantially round region or square or rectangular or hexagonal region, wherein square or rectangular shapes are advantageous with regard to optimum area utilization in view of the usually square or rectangular active area of the camera chips. For sensor applications, by contrast, round or hexagonal regions may also afford advantages. Furthermore, provision can also be made for the fiber arrangement to comprise rigid and flexible regions A, B, that is to say that a rigid fiber arrangement in this case forms the region A and has at least one channel in which a flexible fiber bundle is drawn in as an image guide and forms the region B.

In one preferred embodiment for the fiber rod, it is provided that the region C is designed as an opaque, translucent, largely transparent and/or colored separation region, the wall thickness C of which, depending on the transmittance of the separation region for the wavelength range of the light source, is dimensioned in such a way that stray light transfers between the regions A and B are damped by at least a factor of >10, preferably by a factor of >20.

The inventors have recognized that as a result of the embodiment of the fiber arrangement as a fiber rod in which the individual fibers are fused to one another and/or sintered to one another and/or adhesively bonded to one another at least in partial regions of their outer circumferential surfaces, the probability of crosstalk of guided light from one individual fiber to the next increases. Consequently, it is also possible that, in the operating state, light guided in the region A and/or light reflected from the object at the distal end and reflected back in the region A undergo(es) crosstalk to the region B responsible for guiding the image information. Such light undergoing crosstalk can lead to significant deteriorations in image quality and render examinations impossible. This is a fundamental disadvantage of the fiber rod due to the simplified production method. If the region C is designed as it were as an intermediate region between the regions A and B as described, said region C ensures in a surprisingly simple way that such crosstalk phenomena are at least significantly reduced, as a result of which the image quality achievable by the illumination system according to the invention is improved.

If the region C is designed as opaque, a wall thickness C of a few µm is already sufficient. In the case of a substantially transparent separation region, the latter must generally be made thicker. In particular colored separations have proved to be advantageous here, which act on the one hand as opaque separation or as color filters.

Moreover, opaque fiber elements that absorb stray light between the individual fibers can enhance the contrast.

Regarding the robustness and in particular with regard to the chemical resistance and also with regard to the temperatures that occur in reconditioning cycles by means of autoclaving, it is particularly advantageous if the individual fibers of the fiber arrangement comprise optical fibers, comprising a core glass and a cladding glass. Glass systems having high transmission values in the visible, in particular in the blue spectral range below 520 nm and/or in the near IR range up to 1000 nm additionally afford the advantage that, on the one hand, it is possible to efficiently transmit blue light with high intensity for applications in the field of dental medicine for the curing of dental fillings. In particular important is a high transmission efficiency in the wavelength range of 380 nm to 510 nm especially considering the optimum absorption of the resin material of the dental filling at 380 nm to 390 nm, 460 nm to 470 nm and/or 490 nm to 520 nm. In addition, light losses in the overall system owing, in particular, to shading in the center can be at least partly compensated for. On the other hand, a high transmission in the near IR range also enables applications in which e.g. an image can be recorded by the usual IR detector in the range of 850 nm to 950 nm. This is advantageous for specific applications in the field of medical technology and also in the industrial sphere.

If core glass and cladding glass and also the separation region glass in the region C consist of a lead- or heavy-metal-free glass composition, future RoHS requirements can additionally be satisfied as well. An arrangement comprising quartz fibers is as well conceivable, whereby in particular applications in the UV and/or IR range can be addressed.

Examples of such glasses for the core glass are systems from the field of lead-free silicate-tin glasses which comprise the following components (indicated in % by weight on the basis of oxide):

|  | from | to |
|---|---|---|
| $B_2O_3$ | 0 | 24 |
| $SiO_2$ | 23 | 62.1 |
| $Al_2O_3$ | 0 | 10 |
| $Li_2O$ | 0 | 10 |
| $Na_2O$ | 0 | 18.5 |
| $K_2O$ | 0 | 25.7 |
| BaO | 0 | 57.8 |
| ZnO | 0 | 40 |
| $La_2O_3$ | 0 | 25 |
| $ZrO_2$ | 0 | 10 |
| $HfO_2$ | 0 | 14.2 |
| $SnO_2$ | >0 | 2 |
| MgO | 0 | 8 |
| CaO | 0 | 8 |
| SrO | 0 | 24.4 |
| $Ta_2O_5$ | 0 | 22 |
| $Y_2O_3$ | 0 | 11.9 |
| $Rb_2O$ | 0 | 15 |
| $Cs_2O$ | 0 | 21 |
| $GeO_2$ | 0 | 7.5 |
| F | 0 | 2 |
| $\Sigma R_2O$ | 5 | 20 |
| $\Sigma$ MgO, CaO, SrO, ZnO | 20 | 42 |

The cladding glass or the separation region glass in the region C is preferably constructed from one of the following groups 1 to 4, which each comprise components below (indicated in % by weight on the basis of oxide), wherein the separation region in the region C can be an e.g. black or brown colored cladding glass or enveloping glass having this composition.

|  | Group 1 | Group 2 | Group 3 | Group 4 |
|---|---|---|---|---|
| $SiO_2$ | 70-78 | 63-75 | 75-85 | 62-70 |
| $Al_2O_3$ | 5-10 | 1-7 | 1-5 | 1-10 |
| $B_2O_3$ | 5-14 | 0-3 | 10-14 | >15 |
| $Li_2O$ | 0-2 | 0-1 | 0-3 | 0-2 |
| $Na_2O$ | 0-10 | 8-20 | 2-8 | 0-10 |
| $K_2O$ | 0-10 | 0-6 | 0-1 | 0-10 |
| MgO | 0-1 | 0-5 | 0 | 0-5 |
| CaO | 0-2 | 1-9 | 0 | 0-5 |
| SrO | 0-1 | 0 | 0 | 0-5 |
| BaO | 0-4 | 0-5 | 0 | 0-5 |
| F | 0-1 | 0-1 | 0 | 0-1 |
| Cl | 0-1 | 0-1 | 0 | 0-1 |
| $Fe_2O_3$ | 0-2 | 0-2 | 0-2 | 0-2 |

A corresponding fiber arrangement can also comprise quartz fibers, wherein a quartz fiber comprises a so-called cladding made of organic materials. Such fiber arrangements afford advantages in particular in the transmission of light in the UV or IR range.

It can also be advantageous if the region A and the region B comprise differently transmissive light guiding systems, which can have a different glass composition. In this regard, the individual fibers for the region A can be selected for the light wavelength range optimized for illumination, e.g. blue light or UV light, and the individual fibers of the region B comprise fibers which are optimized for a different region of the spectrum, e.g. for the IR range.

For applications in the range of relatively low temperatures, however, alternatively the individual fibers can also comprise optically conductive plastic fibers, e.g. of polycarbonate or PMMA, which may afford advantages with regard to the production costs.

In one preferred embodiment variant, provision can be made for the fiber rod to have at least one bend and/or one taper between the proximal and distal ends of the fiber rod or to be designed as a spatially deformed fiber rod which can have a varying cross section along its longitudinal axis. Such geometries are used in particular in the dental sector for curing devices, such as were mentioned in the introduction, or for light guides in turbine housings. The bend allows, for example, molars to be able readily to be reached in the oral cavity. With a taper of the fiber rod, the light can be concentrated on smaller regions and the intensity can thus be increased.

For focusing the reflective light from the object surface into the region B of the fiber rod, the optical element at the distal end is designed as a gradient-index lens, a spherical lens, an aspherical lens, a Fresnel lens or as an LSR lens. Gradient-index lenses can be mounted as a very compact cylindrical assembly in the fiber rod end and qualitatively allow a sufficiently good imaging. In contrast to those spherical lenses are inexpensive to produce Aspherically ground lenses have high quality. Such lenses can be produced in particular from Pb- or heavy-metal-free glasses. So-called LSR lenses are also conceivable, which consist of a highly transparent silicone and which can be produced beforehand by means of injection molding and be adhesively bonded or injection-molded directly onto the distal end of the fiber rod.

It is particularly advantageous for the optical element to be embedded into a cover plate, preferably produced from glass, which, by means of an optical adhesive, is fixed to the distal end of the fiber arrangement or of the fiber rod or is adhesively bonded in a hole, designed here as a blind hole, of the fiber rod. The optical adhesive having a refractive index matched to that of the core material of the individual fibers makes it possible that reflection losses can be largely reduced. Moreover, a mechanical processing (grinding and polishing) of the cover sheet with the optical element can be carried out separately from the processing of the fiber rod. Said cover plate is adhesively bonded onto the fiber rod end after surface grinding and polishing have been carried out. What can also be achieved through a suitable choice of adhesive is that it is possible to reduce stray light between the light guiding regions and the image guiding regions. Especially colored adhesives applied on the lateral surface of the optical element are suitable for this purpose. Separate cylindrical sleeves made of metal or opaque plastic between optical element and cover sheet are also conceivable for suppressing stray light.

For effectively coupling out the image, it has proved to be advantageous if the optical coupling element comprises a beam splitter, into which the light from the light source is coupleable via a focusing element in the form of a lens arrangement and/or a reflector and the light collimated in this way can be coupled into the proximal end of the fiber rod, and the image at the proximal end of the fiber rod from the region of the fiber rod with a smaller individual fiber core diameter is projectable onto an active area of the camera by means of a lens system.

In order to improve an imaging of the object surface and primarily to prevent overexposureing the camera, in one preferred embodiment variant, provision can be made for the light source for illuminating an object with the object surface thereof to comprise an LED type A and additionally an LED type B having a different light emission than the LED type A in operating state, and the optical coupling element comprises, at the projection output thereof to the camera, an optical filter having a transmission characteristic for transmitting the light emitted by the LED type B in operating state. It is thereby possible to filter in particular disturbing reflections at the beam splitter, caused by the light from the main light source having the LED type A. In the selection of the LED types A, B, care should be taken in particular to ensure that the emitted spectral ranges of the LED types A and B as far as possible do not overlap and the filter, with regard to its transmission response, is designed as a narrowband color filter having high separation efficiency.

In this case, e.g. for an application in a dental curing device, provision is made for the light source to comprise an LED type A having a radiation spectrum of <520 nm and an LED type B having a radiation spectrum in the green (approximately at 550 nm), yellow (approximately at 580 nm to 600 nm) or red visible spectral range (approximately between 630 nm and 780 nm) or in the IR spectral range. It should be noted here that for applications in the field of IR detection or IR monitoring, the LED type A also emits in the NIR range, e.g. between 800 nm and 1000 nm, and the LED type B emits e.g. in the red visible spectral range between 630 nm and 780 nm. In principle, other LED combinations are also conceivable, depending on the application.

With regard to an application in which contact between the fiber rod and the object surface to be observed at the same time is important, it can advantageously that the fiber rod with its regions A, B and C and the optical element comprises an optical spacer at its distal end, wherein the optical spacer can be designed as a sleeve or tube or as a transparent body, consisting of glass, quartz or plastic, in particular as a light guiding element. Such a requirement is obtained, for example, when the fiber rod for curing the tooth filling is brought into contact with the tooth to be treated in the dental region and at the same time the image of the entire tooth surface is to be detected. This can be ensured by the optical spacer. The invention provides, as the preferred use of the illumination system as described above, use in an inspection system for monitoring equipment or machinery. It is thus possible to realize less complex imaging monitoring instruments in particular for use in harsh environments, e.g. at elevated temperatures, moisture and/or dirt occurrence, in which a resolution in the range of typically 5 µm to 10 µm pixel size is sufficient. A further preferred field of application provides use for an endoscopic instrument in the field of medical technology or for a curing device for dental fillings in the field of dental technology or for an otoscopic application. Here the advantage is afforded, in particular, that such fiber arrangements or fiber rods can protect the sensitive camera part and easily be demounted for medical reconditioning and be mounted again later. Moreover, this also results in electrical isolation between electrically conductive parts and the tissue or the surface to be treated. Interchangeability in the case of a defect is as well also facilitated as a result.

A further application in the medical application field relates to an optical biopsy application, in which a fluorescence image of the tissue surface to be examined can be analyzed. In this case, the tissue surface is irradiated with light of a specific wavelength, e.g. in the blue or near UV range or alternatively in the infrared range of the spectrum depending on the application, and a fluorescence is excited thereby. Said fluorescence image can then be evaluated by means of the camera or a sensor. Tissue changes, for example, can thus be detected at an earlier stage. Further advantageous uses arise in the case of industrial adhesive curing by means of UV light. In this case, positioning monitoring can be realized, for example.

Such a system can as well advantageously be used also in the case of laser welding on workpiece surfaces that are difficult to access. An additional inspection function can thus be realized. Generally, any applications in connection technology are possible with the illumination system according to the invention, in particular including inspection of riveted connections and/or generally in adhesive-bonding technology.

A further advantageous field of application is for analytical purposes, in this case in particular the monitoring and/or testing of liquid substances. With the illumination device according to the invention, it is possible, for example, to identify and/or to quantify the presence of bodies, e.g. suspended matter, in liquids and/or gases. By way of optical methods, in particular, it would even appear to be possible to characterize and/or identify said bodies. Accordingly, one preferred field of application is water monitoring, including process steps for treatment of drinking water.

BRIEF DESCRIPTION OF THE DRAWING

The invention is explained in greater detail below on the basis of an exemplary embodiment illustrated in the figures, in which:

FIG. 4 shows one specific embodiment of the coupling-out end of the fiber rod, and FIGS. 5a and 5b schematically show the size ratio between the active area of the camera and that region of the fiber rod which is provided for image guiding.

DETAILED DESCRIPTION

Figure 1:
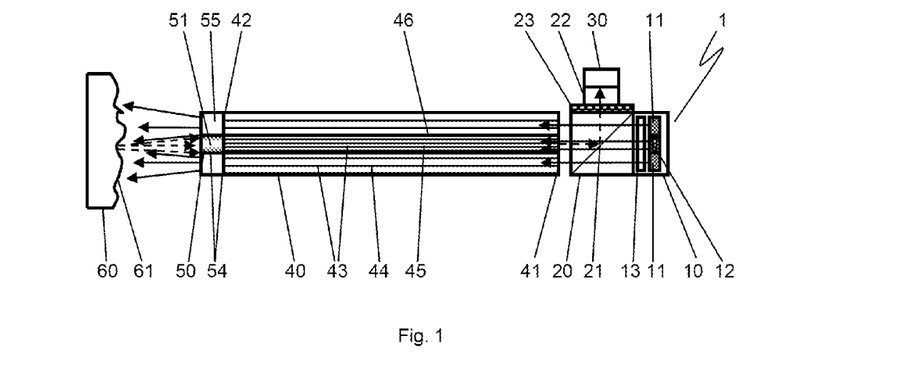
FIG. 1 schematically shows an illumination system comprising a fiber rod.

FIG. 1 schematically shows the construction of an illumination system 1 according to the invention. A rigid fiber arrangement in the form of a fiber rod 40 is illustrated here by way of example.

In the example shown, the illumination system 1 comprises a light source 10, which as an LED light source is equipped with predominantly an LED type A 11, which emits light in a specific spectral range. In addition, a second LED type B 12 can optionally also be arranged in the light source 10, said second LED type B emitting light in a second spectral range.

For a curing device for dental fillings, by way of example, the LEDs of the LED type A 11 are designed as LEDs exhibiting blue light emission. The wavelength of the blue light is usually between 390 nm and 520 nm and in this case is coordinated in particular with the reaction kinetics of the dental filling material. The wavelength of the LEDs of the LED type B 12 can be for example in the green or red visible spectral range and ideally has no overlap with the spectral range of the LED type A 11.

For other applications, the LEDs of the LED type A 11 can also be designed as white light LEDs, wherein the LEDs of the LED type B 12 in this case can also emit in the NIR range, for example between 800 nm and 1000 nm.

The light from the light source 10 is coupled via a focusing element 13 into an optical coupling element 20 into the proximal end 41 of the fiber rod 40. In this case, the focusing element 13 can be designed as a lens arrangement and/or a reflector. Light guiding rods which serve for light mixing and thus enable light to be coupled in more homogeneously are likewise conceivable as well.

The optical coupling element 20 comprises a beam splitter 21, by means of which light reflected back from the fiber rod 40 can be coupled out laterally to a camera 30.

The fiber rod 40 having a diameter of typically 6 to 12 mm consists of a fiber arrangement having several thousand individual fibers 43, which are aligned substantially parallel to one another, wherein according to the invention the fiber rod has a region A 44 having individual fibers 43 that serve for light guiding, in particular, and have an individual fiber core diameter A 44.1 that is usually in the range of 40 to 100 µm. In the center of the fiber rod 40, the fiber rod 40 has a region B 45, in which the individual fibers 43 have an individual fiber core diameter B 45.1 in the range of 10 to 20 µm, preferably of less than 10 µm, depending on the fiber drawing method. Said region B 45 serves as an image guide and is separated from the region A 44 by a region C 46.

An optical element 50 is fitted at the distal end 42 of the fiber rod 40, said optical element focusing the reflected-back light from an object surface 61 of an object 60 to be inspected and coupling it into the region B 45 of the fiber rod 40. In the example shown, the optical element is designed as a cylindrical gradient-index lens 51 (also known as GRIN lens), which is positioned in a cover plate 55 made of glass or transparent plastic in a manner centered with respect to the region B 45 of the fiber rod 40. The gradient-index lens 51 and the cover sheet 55 are adhesively bonded to the fiber rod 40 by means of an optical adhesive 54, usually a highly transparent and thermally stable two-component epoxy resin adhesive.

The image information guided by means of the optical element 50 in the region B 45 of the fiber rod 40 is projected at the proximal end 41 of the fiber rod by way of the beam splitter 21 to the camera 30 by means of a lens system 22. In order to suppress reflections of the generally intensive light of the LEDs of the LED type A 11, a filter 23 is provided upstream of the camera 30, which filter allows only the light from the LEDs of the LED type B 12 to pass.

Figure 2:
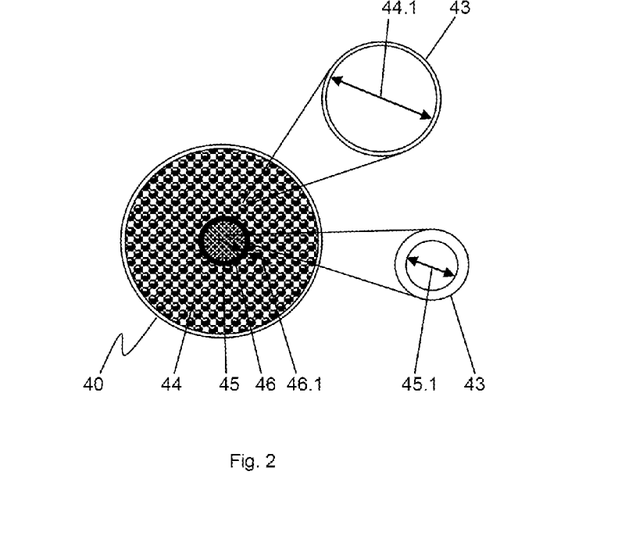
FIG. 2 shows a cross section through the fiber rod.

FIG. 2 shows the cross section of the fiber rod 40 having the regions A, B and C 44, 45, 46. The different individual fiber core diameters A, B 44.1, 45.1 of the individual fibers 43 are illustrated schematically, in a manner not true to scale, this also being referred to as active fiber area. In this case, provision can be made for the ratio between the individual fiber core diameter B 45.1 and the diameter of the individual fibers 43 in the region B 45 to be less than the ratio between the individual fiber core diameter A 44.1 and the diameter of the individual fibers 43 in the region A 44. During the production process, this prevents the cladding thickness of the individual fibers 43 from becoming too thin and prevents the occurrence of losses of contrast or adverse effects on the image information transmission as a result. The region A 44 is spaced apart from the region B 45 by a region C 46, which has a specific wall thickness 46.1 dimensioned such that as far as possible no exchange of stray light occurs between the regions A and B 44, 45. To that end, provision can be made for the region C 46 to comprise an opaque, translucent and/or colored material acting as a filter layer.

These figures like all the rest of the drawings are purely schematic. Real size relationships cannot be gathered from them. Particularly with the use of glass materials as fiber material of the fiber rod, the fibers advantageously fuse and/or sinter at their outer circumferential surfaces as they are being drawn. The cross section of the individual fibers usually approximates to a hexagonal shape.

Figure 3A:
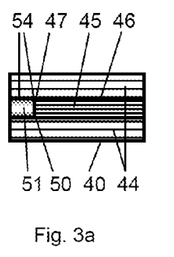
FIGS. 3a to 3c show various exemplary embodiments of an optical element at the coupling-out end of the fiber rod.
Figure 3B:
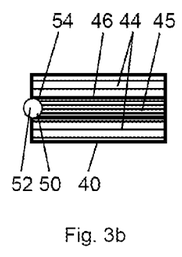
Figure 3C:
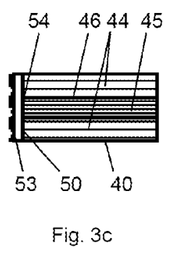

FIGS. 3a to 3c show various exemplary embodiments of the optical element 50. The optical element 50 has the task of focusing the light from the object surface 61 of the object 60 to be inspected and of coupling the image into the region B 45 of the fiber rod 40. Converging lenses are therefore used here.

In FIG. 3a, the gradient-index lens 51 as optical element 50, as already shown in FIG. 1, is directly integrated into the end of the fiber rod 40. For this purpose, a hole 47 is provided in the region B 45, the gradient-index lens 51 being adhesively bonded into said hole by means of the optical adhesive 54.

FIG. 3b shows a spherical lens 52 as optical element 50, said spherical lens being adhesively bonded into a corresponding spherical depression of the fiber rod 40 in the region of the region B 45 by means of the optical adhesive.

In FIG. 3c, the optical element 50 is carried out as a Fresnel lens 53, which can have, on the surface thereof, different ring-shaped structures for focusing the light reflected back from the object surface 61 and alternatively for focusing the light onto the object surface 61 to be inspected. Ideally, said Fresnel lens 53 is carried out as a pressed glass or plastic sheet and is adhesively bonded onto the fiber rod 40 by means of the optical adhesive 54.

Figure 4:
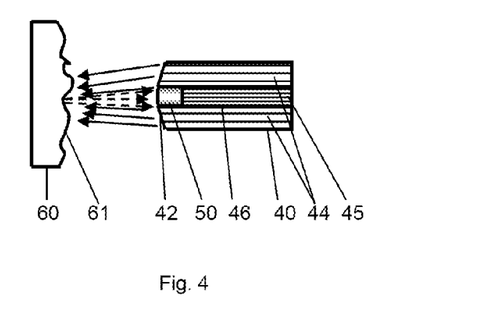

In one preferred embodiment variant of the fiber rod 40, provision can be made, as shown in FIG. 4, for the distal end 42 of the fiber rod 40 in the region A 44 to be finish-processed slightly obliquely or "convexly". Thus it can be achieved that the light which is guided via the fibers in the region A 44 is diffracted with respect to the center axis of the fiber rod 40 upon emerging from the fiber rod 40, which entails a focusing and homogenizing effect. The light shading by the region B 45 on the object surface 61 can therefore be at least partly compensated for.

Figure 5A:
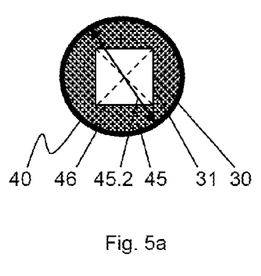

With regard to the design of the diameter B 45.2 of the region B 45 with respect to the active area 31 of the camera 30 or of the sensor, FIG. 5a shows that the diameter B 45.2 of the region B 45 corresponds at a minimum to the diagonal of the usually square or rectangular camera chip plus a tolerance reserve required for the positioning. Given an active area 31 of 1×1 mm, this results in a minimum diameter B 45.2 of the region B 45 of approximately 2.0 to 2.5 mm if a figure of 0.3 to 0.5 mm is assumed as positioning tolerance.

Figure 5B:
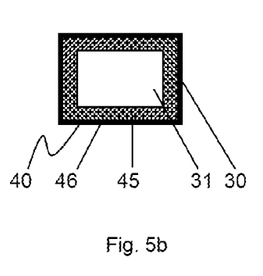

FIG. 5b shows the situation as illustrated in FIG. 5a in the case of a rectangular region B 45 of the fiber rod 40. The dimensioning of the region B 45 is designed here to be larger than the active area 31 of the camera 30 or of the sensor by approximately 0.3 to 0.5 mm all around the perimeter.

With regard to avoiding disturbing stray light between the region A 44 and the region B 45, the region C 46 is provided, for which purpose a black colored enveloping glass between the regions A and B 44, 45 is used as a separation region that absorbs stray light. It is furthermore conceivable to introduce opaque colored fiber elements between the individual fibers 43. It is thus possible to achieve an enhancement of contrast owing to the avoidance of stray light between the individual fibers 43.

In principle, for specific applications, two or a plurality of regions B 45 within the fiber arrangement or the fiber rod 40 are also conceivable, e.g. a first region B 45 for image transmission and a further region B 45, arranged in a manner spatially separated from the first region B 45, for the transmission of a sensor signal.

Figure 6:
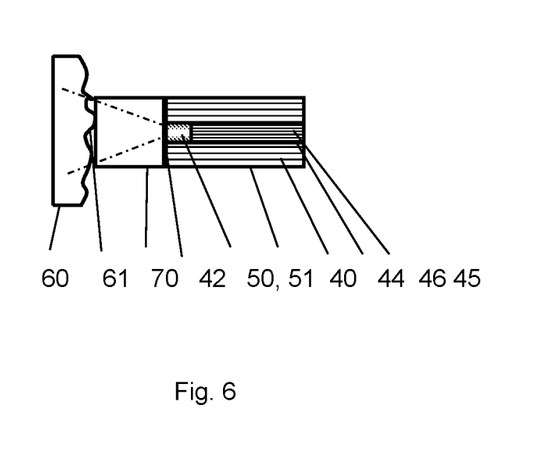
FIG. 6 shows an arrangement in which the fiber rod has regions and an optical element at a distal end.

FIG. 6 shows an arrangement in which the fiber rod 40 with its regions A 44, B 45 and C 46 and the optical element 50 at its distal end 42, which in the illustrated example is embodied as a gradient index lens (GRIN lens) 51, comprise an optical spacer 70, wherein the optical spacer can be designed as a transparent, translucent or opaque sleeve or tube or as a transparent body, consisting of glass, quartz or plastic (eg of PC, PMMA), in particular as a light guiding element and/or a combination thereof. The fiber rod 40 can be brought into contact with the object surface 61 of the object 60, whereby an image of the object surface 61 covered by the cross-section of the spacer can be simultaneously recorded A sensor, e.g. an IR or UV sensor, can also be arranged instead of the camera 30. Such a sensor can have different zones, for example, wherein a spatial signal evaluation is made possible by means of the fiber arrangement. Particularly with the use of the glass compositions described above, a UV application can be made possible in the near UV range (typically 350 nm to 400 nm).

The illumination device according to the invention has the advantage that it is producible with reduced production outlay and, compared with the endoscopic solutions from the prior art, although said illumination device provides a reduced image quality, in view of the low production outlay the image quality is good enough to enable diverse applications even in high numbers.

LIST OF REFERENCE NUMERALS:

| | |
|---|---|
| 1 | Illumination system |
| 10 | Light source |
| 11 | LED type A |

-continued

LIST OF REFERENCE NUMERALS:

| | |
|---|---|
| 12 | LED type B |
| 13 | Focusing element |
| 20 | Optical coupling element |
| 21 | Beam splitter |
| 22 | Lens system |
| 23 | Filter |
| 30 | Camera |
| 31 | Active area |
| 40 | Fiber rod |
| 41 | Proximal end |
| 42 | Distal end |
| 43 | Individual fiber |
| 44 | Region A |
| 44.1 | Individual fiber core diameter A |
| 45 | Region B |
| 45.1 | Individual fiber core diameter B |
| 45.2 | Diameter of region B |
| 46 | Region C |
| 46.1 | Wall thickness C |
| 47 | Hole |
| 50 | Optical element |
| 51 | Gradient-index lens (GRIN lens) |
| 52 | Spherical lens |
| 53 | Fresnel lens |
| 54 | Adhesive |
| 55 | Cover sheet |
| 60 | Object |
| 61 | Object surface |
| 70 | Optical spacer |

What is claimed is:

1. An illumination system, comprising:
an optical element; and
at least one spatial fiber arrangement formed from a multiplicity of individual fibers and having a distal end and a proximal end, the multiplicity of individual fibers being separated into a first region (A), a second region (B), and a third region (C), the first region (A) being separated from the second region (B) by the third region (C), the individual fibers in the second region (B) having a smaller active diameter in comparison with the individual fibers of the first region (A), the optical element being at the distal end and being assigned to at least to the second region (B), the individual fibers in the first, second, and third regions (A, B, C) are joined so that the fiber arrangement is a rigid fiber rod, the individual fibers in the third region (C) suppressing stray light transfers between the first and second regions (A, B).

2. The illumination system as claimed in claim 1, wherein the individual fibers are fused to one another at least in partial regions of outer circumferential surfaces.

3. The illumination system as claimed in claim 1, wherein the individual fibers are sintered together at least in partial regions of outer circumferential surfaces.

4. The illumination system as claimed in claim 1, wherein the individual fibers are adhesively bonded to one another at least in partial regions of outer circumferential surfaces.

5. The illumination system as claimed in claim 1, further comprising an optical coupling element at the proximal end, the optical coupling element being configured to couple light into the rigid fiber rod and configured to couple an image from the second region (B) into a camera and/or into a sensor.

6. The illumination system as claimed in claim 1, the individual fibers in the second region have a core diameter of less than 25 μm.

7. The illumination system as claimed in claim 1, wherein the third region (C) has a property selected from the group consisting of opaque, translucent, transparent, and colored and has a wall thickness dimensioned so that stray light transfers between the first and second regions (A, B) are damped by at least a factor of 10.

8. The illumination system as claimed in claim 1, further comprising opaque fiber elements that absorb stray light positioned between the individual fibers.

9. The illumination system as claimed in claim 1, wherein the individual fibers are optical fibers comprising a core glass and a cladding glass.

10. The illumination system as claimed in claim 9, wherein the core glass and the cladding glass comprise a lead-free or heavy-metal-free glass composition.

11. The illumination system as claimed in claim 9, wherein the individual fibers in the third region (C) comprise a lead-free or heavy-metal-free glass composition.

12. The illumination system as claimed in claim 1, wherein the individual fibers are quartz fibers.

13. The illumination system as claimed in claim 1, wherein the individual fibers have high transmission values in the blue visible spectral range below 520 nm and/or in the near IR range up to 1000 nm.

14. The illumination system as claimed in claim 1, wherein the individual fibers consist of optically conductive plastic fibers.

15. The illumination system as claimed in claim 1, wherein the rigid fiber rod has at least one bend and/or one taper between the proximal and distal ends.

16. The illumination system as claimed in claim 1, wherein the rigid fiber rod has a varying cross section along a longitudinal axis between the proximal and distal ends.

17. The illumination system as claimed in claim 1, wherein the optical element is selected from the group consisting of a gradient-index lens, a spherical lens, an aspherical lens, a Fresnel lens, and an LSR lens.

18. The illumination system as claimed in claim 1, wherein the optical element is embedded in a cover plate by an optical adhesive.

19. The illumination system as claimed in claim 1, wherein the optical element is adhesively bonded in a hole of the rigid fiber rod.

20. The illumination system as claimed in claim 1, wherein the proximal end is configured so that collimated light is coupled into the proximal end so that an image at the proximal end from the second region (B) is projectable at the distal end through a lens system onto an active area of a camera and/or of a sensor.

21. An illumination system, comprising:
an optical element;
at least one spatial fiber arrangement formed from a multiplicity of individual fibers and having a distal end and a proximal end, the multiplicity of individual fibers being separated into a first region (A), a second region (B), and a third region (C), the first region (A) being separated from the second region (B) by the third region (C), the individual fibers in the second region (B) having a smaller active diameter in comparison with the individual fibers of the first region (A), the optical element being at the distal end and being assigned to at least to the second region (B), the individual fibers in the first, second, and third regions (A, B, C) are joined so that the fiber arrangement is a rigid fiber rod, the third region (C) suppressing stray light transfers between the first and second regions (A, B); and opaque fiber elements that absorb stray light positioned between the individual fibers.

\* \* \* \* \*